United States Patent [19]

Mayfield

[11] Patent Number: 4,468,221
[45] Date of Patent: Aug. 28, 1984

[54] MEDICATION INFUSION PUMP

[75] Inventor: William B. Mayfield, Costa Mesa, Calif.

[73] Assignee: Parker-Hannifin Corporation, Cleveland, Ohio

[21] Appl. No.: 515,449

[22] Filed: Jul. 20, 1983

Related U.S. Application Data

[63] Continuation of Ser. No. 252,779, Apr. 10, 1981, abandoned.

[51] Int. Cl.³ ............................................. A61M 5/20
[52] U.S. Cl. ............................ 604/152; 128/DIG. 12
[58] Field of Search ............................ 604/151–153, 604/67, 891; 128/DIG. 12, DIG. 13; 417/417

[56] References Cited

U.S. PATENT DOCUMENTS

| | | | |
|---|---|---|---|
| 2,925,814 | 2/1960 | Vibber et al. | 604/152 |
| 3,923,060 | 12/1975 | Ellinwood | 604/891 |
| 3,985,133 | 10/1976 | Jenkins et al. | 604/152 |
| 4,209,014 | 6/1980 | Setton | 604/132 |
| 4,274,407 | 6/1981 | Scarlett | 604/152 |
| 4,373,527 | 2/1983 | Fischell | 128/903 X |

*Primary Examiner*—Dalton L. Truluck
*Attorney, Agent, or Firm*—James A. Baker; Frederick L. Tolhurst

[57] ABSTRACT

An extracorporeal medication infusion device provides a precise infusion rate of a liquid medication into a human or animal body. The infusion device includes a permanent portion which has a case, a battery, a programmable electronic controller, and an electromagnetic solenoid core and solenoid coil for providing an actuation force. The infusion device also includes a disposable portion which includes a reservoir filled with a liquid medication that is to be dispensed and a pump for pumping the medication from the reservoir into the user's body. The pump includes a pump chamber and a piston connected to an electromagnetic armature for altering the volume of the pump chamber in response to the actuation force.

12 Claims, 10 Drawing Figures

MEDICATION INFUSION PUMP

This application is a continuation, of application Ser. No. 252,779, filed Apr. 10, 1981 now abandoned.

BACKGROUND OF THE INVENTION

The present invention relates generally to medication infusion devices, and more particularly to a miniature extracorporeal medication infusion device for precisely and conveniently dispensing controlled quantities of a liquid medicine into a human or animal body.

Liquid medications (which, for purposes of this patent application, means any liquid that is to be injected into a human or animal body for therapeutic or diagnostic purposes) have been traditionally administered by a hypodermic syringe. If multiple doses of the liquid medication are required, the multiple doses are typically administered at timed intervals of several days or several hours.

More recently, it has been recognized that the benefits of certain liquid medications may be enhanced by administering the liquid medication in extremely small dosages on a frequent basis. Medication infusion devices which have been designed for this purpose are disclosed in U.S. Pat. Nos. 4,191,181, 4,150,672, 4,215,689, and 3,858,581. Additionally, other devices have been provided which administer a constant flow rate of liquid medication, such as shown in U.S. Pat. No. 4,201,207.

SUMMARY OF THE INVENTION

The present invention departs from these and other prior art devices by providing an extracorporeal medication infusion device which permits precise control of the dosage of liquid medication that is administered and that provides ease and convenience of use.

According to the principles of the invention, the extracorporeal medication infusion device includes a reusable portion and a disposable portion. The resusable portion includes a rigid case, a battery power supply, and a programmable electronic controller. The reusable portion of the infusion device also includes an electromagnetic solenoid core and an electromagnetic solenoid coil which receives an electrical signal from the controller and provides a magnetic actuating force.

The disposable portion of the infusion device includes a collapsable reservoir for storing the liquid medication. The disposable portion also includes a disposable pump for pumping the liquid medication from the reservoir to the human or animal body to which the liquid medication is to be provided. The pump includes a pumping chamber having inlet and outlet check valves, and an electromagnetic armature provides a means to vary the volume of the chamber in response to the magnetic actuating force of the coil.

The disposable portion and the reusable portion each also include precise alignment surfaces arranged in predetermined positions. When the disposable portion is releasably secured in the case of the reusable portion, the alignment surfaces of the disposable portion engage corresponding alignment surfaces of the reusable portion. In this manner, the armature on the disposable portion is precisely aligned with and spaced a predetermined distance from the core in the reusable portion. When the electrical signal is provided by the controller to the coil, the magnetic force then provides movement of the armature through this predetermied distance. When the electrical signal is terminated, a leaf spring returns the armature to its rest position.

This arrangement of applicant's invention assures that the movement of the armature and corresponding stroke of the pump will always be the same, when the disposable portions are changed on a periodic basis while the device is being used. Additionally, because the pump utilizes the positive action of a leaf spring to return the pump to the rest position at the completion of each pump cycle, the return stroke and output pressure of the pump is also precisely controlled. Still further, the infusion device provided by the instant invention is convenient and easy to use, and provides the option to the use of either filling the reservoir pump from a separate vial of liquid medication or puchasing the disposable portion in a prefilled condition for maximum convenience and ease of use.

BRIEF DESCRIPTION OF THE DRAWINGS

These and other aspects and advantages of the invention will be more readily apparent upon an understanding of the preferred embodiment of the invention shown in the drawings, wherein.

DETAILED DESCRIPTION OF THE DRAWINGS

Figure 1:
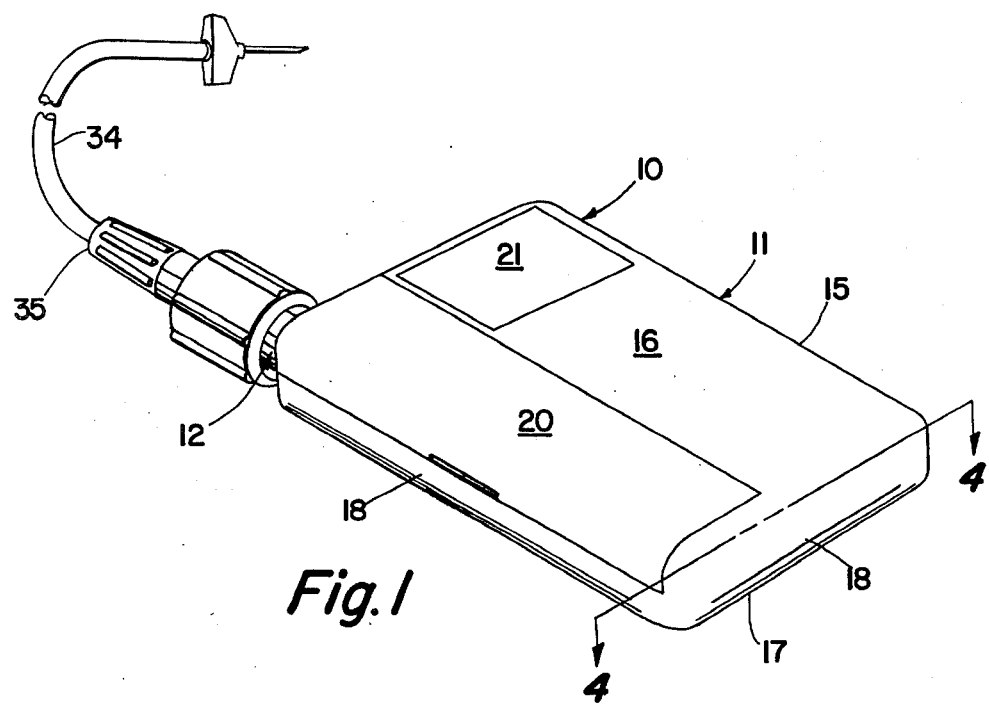
FIG. 1 is a perspective view of the extracorporeal medication infusion device according to the principles of the invention.

Referring now to the drawings in greater detail, FIG. 1 illustrates an extracorporeal medication infusion device 10. The medication infusion device 10 is of small size (approximately 2½ inches long, 1 inch wide, and ½ inch thick) and light weight (approximately 2½ ounces) and is adapted to be carried in the user's pocket or taped or strapped to the user's body. The medication infusion device 10, as explained in further detail below, carries a reservoir of liquid medication and provides a means for dispensing the liquid medication into the user's body at a programmed rate.

Figure 4:
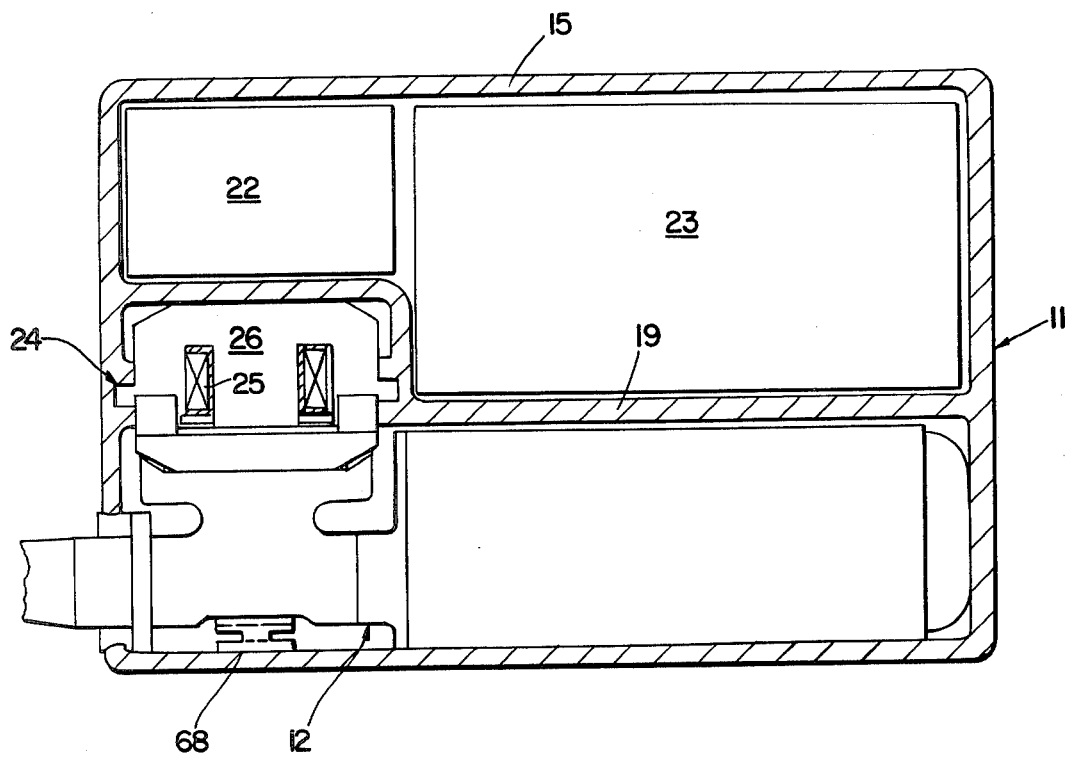
FIG. 4 is a cross-sectional view taken along reference view line 4—4 in FIG. 1.

Referring now to FIGS. 1 and 4 together, the medication infusion device 10 includes a reusable portion 11 and a disposable portion 12. The reusable portion 11 is adapted to be utilized repeatedly over a period of several years for dispensing liquid medication to the body of the user. The disposable portion 12 is adapted to dispense a predetermined quantity of liquid medication which it carries, and to then be discarded and replaced with a new disposable portion carrying a new quantity of the liquid medication.

Referring still to FIGS. 1 and 4, the reusable portion 11 includes a rigid plastic case 15. The case 15 includes a top wall 16, a bottom wall 17, end walls 18, and internal dividing walls 19. The walls 16–19 are all of approximately the same thicknesss and same material. The top wall 16 includes a removable panel 20 for providing access to the disposable portion 12 and a removable panel 21 for providing access to a battery 22 which provides a source of electrical power for the medication infusion device 10. The removable panels 20 and 21 are secured in place by a suitable detent (not shown) in a well known manner.

The reusable portion 11 also includes a programmable electronic controller 23 which receives electrical power from the battery 22 and which provides electrical energy to a solenoid 24.

Figure 10:
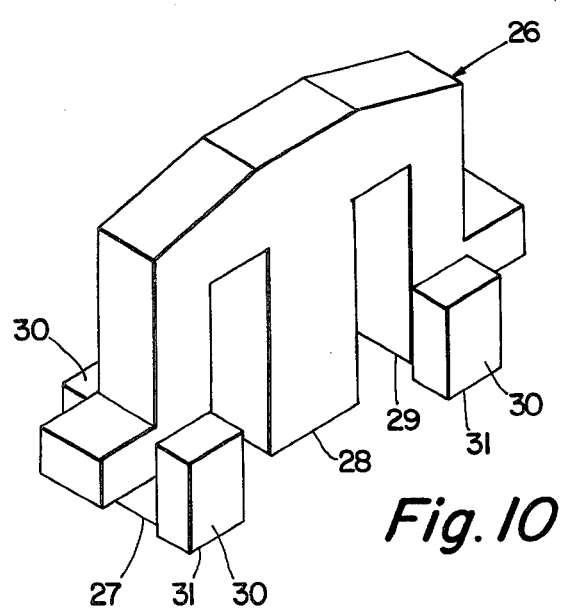
FIG. 10 is an enlarged perspective view of the solenoid core for the reusable portion of the device shown in FIG. 4.

The solenoid 24 includes a coil 25 which is energized by the controller 23 on a programmed basis and an electromagnetic core 26. The core 26, as shown in greater detail in FIG. 10, is made of magnetic material (such as a martensitic stainless steel) and is of a generally E-shaped configuration. The core 26 includes end walls 27, 28 and 29 which face toward an armature as explained in greater detail below. The end walls 27 and 28 are coplanar, and the end wall 28 may be recessed slightly from the plane in which the walls 27 and 29 are disposed to facilitate release of the armature after actuation of the coil 25.

Four identical alignment bars 30, only three of which may be seen in FIG. 10, are secured at similar locations on opposite sides of the core 26. The alignment bars 30 are each of non-magnetic material (such as an austenitic stainless steel) and are welded to the core 26 in the position shown in FIG. 10. The alignment bars 30 each include a precise alignment surface 31, and the alignment surfaces 31 are co-planar. The plane in which the alignment surfaces 31 are disposed is spaced a predetermined distance from the plane in which the core surfaces 27 and 29 are disposed, and the perpendicular distance between these two planes is the stroke of the pump, as explained in further detail below.

Referring back to FIG. 1, the medication infusion device 10 also includes a replaceable needle and connecting tube assembly 34. The assembly 34 is connected to the disposable portion 12 by a threaded connection 35. The needle and connecting tube assembly 34 may therefore be disconnected from the disposable portion 12 when the disposable portion 12 is to be replaced.

Figure 2:
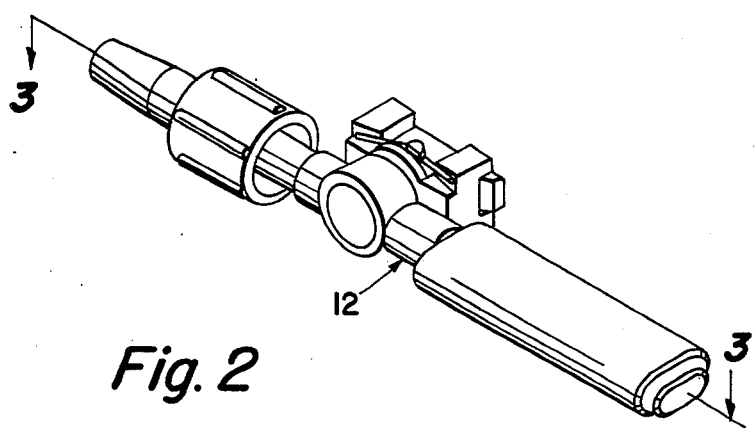
FIG. 2 is a perspective view of the disposable portion of the device shown in FIG. 1.
Figure 3:
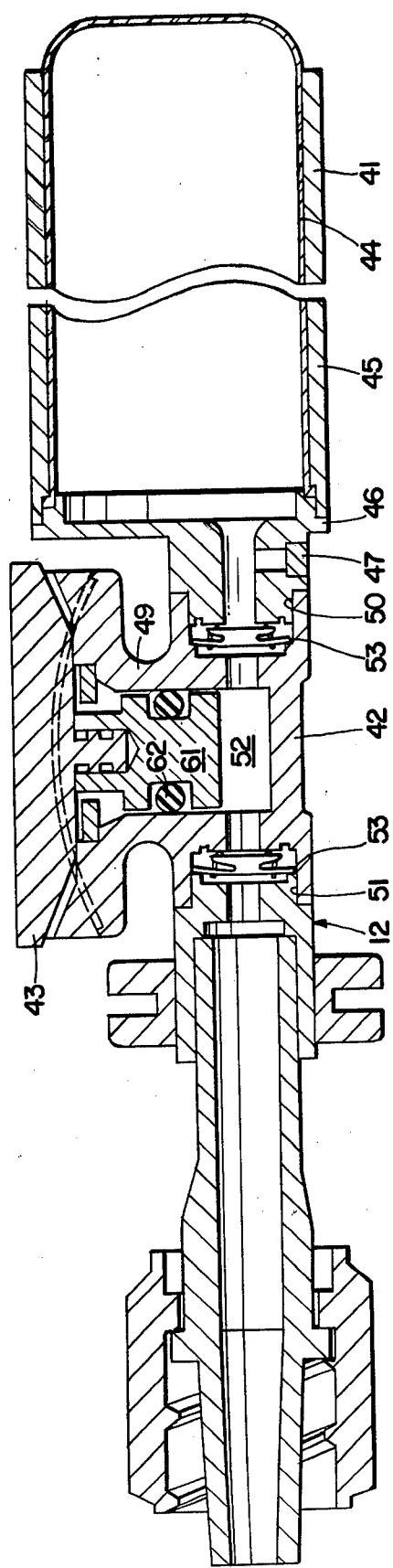
FIG. 3 is an enlarged cross-sectional view taken along reference view line 3—3 in FIG. 2.

Referring now to FIGS. 1, 2 and 3 together, the disposable portion 12 includes a reservoir 41, a pump 42, and an electromagnetic armature 43. The reservoir 41 includes a collapsable plastic bag 44 that is secured within a cylindrical plastic housing 45 and sealingly attached to a plastic end wall 46. The collapsable bag 44 is filled by injecting the liquid medicine that is to be dispensed through a septum 47.

Figure 6:
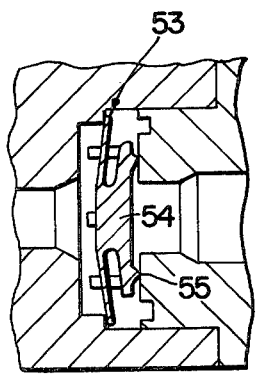
FIG. 6 is an enlarged view of the inlet check valve shown in FIG. 3.
Figure 7:
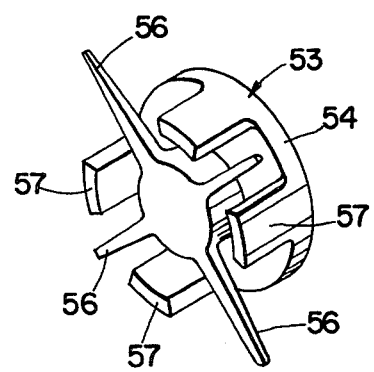
FIG. 7 is a still further enlarged perspective view of the check valve shown in FIG. 6.

The pump 42 includes a pump housing 49 which defines an inlet passage 50, an outlet passage 51, and a pump chamber 52. The pump 42 also includes check valves 53 placed in the inlet and outlet passages 50 and 51. The check valves 53, as shown in greater detail in FIGS. 6 and 7, are of one-piece plastic construction and include a base 54. In the preferred embodiment, the check valves are of a thermoplastic carbonate linked polymer such as that sold under the trademark "Lexan" by General Electric Co., or of an acrylic polymer resin such as that sold under the trademark "Cryolite G-20" by Cry/Ro Industries. An annular seat 55 projects from one side of the base 54 to provide sealing engagement with an adjacent surface in the passage. A plurality of leaf spring portions 56 project from a central hub of the base 54 and provide a spring force to urge the seat 55 against its adjacent surface. A plurality of axially extending stops 57, which are disposed between adjacent ones of the springs 56, project from the base 54 in a direction opposite to the seat 55 to control the travel of the seat 55 away from its adjacent surface when the check valve 53 is opened.

Figure 8:
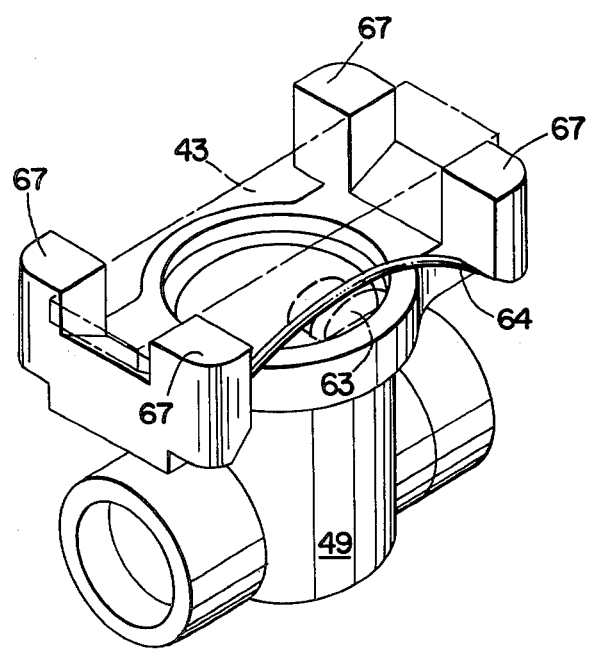
FIG. 8 is an enlarged perspective view of the pump housing for the device, with the armature shown in phantom.
Figure 9:
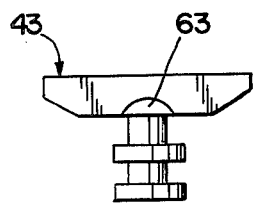
FIG. 9 is a side-elevational view of the armature for the disposable portion shown in FIG. 2.

Referring now to FIGS. 3, 8 and 9 together, the pump 42 further includes a piston 61 which reciprocates in a bore that intersects the pump chamber 52 in a direction perpendicular to the axis of the passages 50 and 51. The piston 61 is of plastic construction and is sealed against the walls of the bore in which it is disposed by an o-ring seal 62. The o-ring seal 62 is dimensioned and arranged so that it is compressed in the groove in the outer peripheral surface of the piston 61 and so that it does not slide relative to either the piston 61 or the bore. Instead, the o-ring 62 is of sufficient elasticity, and the movement of the piston 61 is sufficiently small, that elastic deformation of the o-ring 62 is sufficient to accommodate the full stroke of the piston 61 in the bore.

The electromagnetic armature 43, which is of magnetic material such as martensitic stainless steel, includes a stem portion projecting from its bottom surface which is received with an interference fit in a bore in the piston 61. In this manner, the armature 43 is rigidly connected to the piston 61 so that movement of the armature 43 causes corresponding movement of the piston 61. Two suitable spring rests 63, only one of which is shown in FIGS. 8 and 9, project laterally in opposite directions from the armature 43. Two identical leaf springs 64 are provided on each lateral side of the pump housing 49 and act between the pump housing 49 and the spring rests 63 to urge the piston 61 to its rest position shown in the drawings.

As best shown in FIG. 8, the pump housing 49 also includes alignment surfaces 67. The alignment surfaces 67 are co-planar with one another and are co-planar with the top surface of the armature 43. When the pump 42 is manufactured, this co-planar relationship may be accomplished by initially making the alignment surfaces 67 project beyond the top surface of the armature 43, and then, after the armature 43 and springs 64 are installed in the pump housing 49, melting or grinding the surfaces 67 to a co-planar relationship with the top surface of the armature 43.

Figure 5:
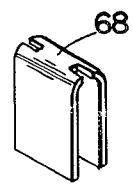
FIG. 5 is a perspective view of a spring that is used to maintain alignment of the disposable portion and the reusable portion of the device shown in FIG. 1.

Referring now to FIGS. 3 and 4 together, the disposable portion 12 is releasably assembled in the case 15 by opening the removable panel 20. The disposable portion 12 is then inserted into the case 15 in a manner such that the alignment surfaces 67 of the pump housing 49 (FIG. 8) contact the alignment surfaces 31 of the core 26 (FIG. 10). This contact is established and maintained by a suitable leaf spring 68 (see FIGS. 4 and 5). An elastomeric grommet 69, which is frictionally received in an open ended slot in the case 15 when the cover 20 is removed, secures the removable portion 12 against axial movement relative to the reusable portion 11.

The materials for the reusable portion 11 and disposable portion 12 are selected from commercially available thermoplastic materials to provide adequate strength and rigidity, resistance to chemicals, and ease of manufacturing. In the preferred embodiment, the case 15 is of an acrylonitrile-butadiene-styrene copolymer (ABS), the reservoir 44 is of a suitable flexible thermoplastic urethane resin, and the pump housing 49 and piston 61 are of an acrylic polymer resin such as that sold under the trademark "Cryolite G-20" by Cy/Ro Industries.

When it is desired to pump the liquid medication from the collapsable reservoir 44 to the outlet passage 51 and to the needle and tube assembly 34, the controller 23 provides an electrical current to energize the coil 25. This causes the armature 43 to move upwardly as viewed in the drawings until the top surface of the armature 43 engages the surfaces 27 and 29 of the core 26. This causes the piston 61 to move upwardly to increase the volume of the chamber 52. As the volume of the chamber 52 increases, the check valve 53 in the inlet passage 50 opens to permit liquid medication to flow from the reservoir 44 into the pump chamber 52. When this electrical current is interrupted, the coil 25 is de-energized and the springs 64 push the armature 43 and piston 61 downwardly as viewed in the drawings to decrease the volume of the chamber 52. This causes the check valve 53 in the outlet passage 51 to open to permit flow of the liquid medicine from the pump chamber 52 to the needle and tube assembly 34. When the liquid medication in the reservoir 44 is nearly depleted, the user opens the removable panel 20, removes the existing disposable portion 12, and inserts a new disposable portion 12 with a full reservoir of liquid medication.

What is claimed is:

1. A medication injection device having a reusable portion that includes an electromagnetic solenoid core, a solenoid coil and means for energizing the solenoid coil, said device further including a disposable portion that is releasably secured to said reusable portion said disposable portion comprising:
   a reservoir;
   a pump chamber;
   an electromagnetic solenoid armature that contacts a first engagement surface when said solenoid coil is energized and that is biased against a second engagement surface that is maintained with respect to said first engagement surface when said solenoid coil is de-energized;
   a piston located in said pump chamber and secured to an moveable with said armature, said piston having a first position defining a minimum volume configuration of said pump chamber when said armature is biased against second engagement surface and a second position defining a maximum volume configuration of said pump chamber when said armature contacts said first engagement surface; and
   spring means for resiliently biasing said piston such that said piston is urged toward said first position.

2. The medication injection device of claim 1 further comprising:
   a first alignment surface means that is included in said reusable portion; and
   a second alignment surface means included in said disposable portion that engages said first alignment surface means to precisely position said first engagement surface with respect to said second engagement surface.

3. The medication device of claim 1 wherein said first engagement surface comprises an end wall of said core.

4. The medication injection device of claim 1, 2 or 3 wherein said disposable portion includes spring means for biasing said armature away from said first engagement surface and against said second engagement surface.

5. A medication injection device comprising:
   an electromagnetic solenoid core;
   a solenoid coil;
   first alignment surface means disposed in a predetermined position relative to said solenoid core;
   a reservoir;
   a pump chamber;
   an electromagnetic solenoid armature that is driven against a first engagement surface when said solenoid coil is energized and that is biased against a second engagement surface when said solenoid coil is de-energized;
   a piston located in said pump chamber and secured to an moveable with said armature, said piston having a first position defining a minimum volume configuration of said pump chamber when said armature is biased against said second engagement surface and a second position defining a maximum volume configuration of said pump chamber when said armature contacts said first engagement surface;
   spring means for resiliently biasing said piston such that said piston is urged toward said first position; and
   second alignment surface means disposed in a predetermined position relative to said armature and engaging said first alignment surface means to precisely position said first engagement surface relative to said second engagement surface.

6. The medication injection device of claim 5, wherein said pump chamber is defined by a pump housing, and wherein said second alignment surface means is diposed on the pump housing.

7. The medication injection device of claim 5, further comprising second means that resiliently biases said second alignment surface means against said first alignment surface means.

8. The medication injection device of claim 5, wherein said pump chamber comprises:
   a pump housing;
   inlet and outlet passages in said pump housing connected to said pump chamber; and
   first and second check valves located in said inlet and outlet passages respectively.

9. The medication injection device of claim 8, wherein sid pump chamber includes a pump housing defining a bore with the piston located in said bore said device further comprising:
   annular elastomeric seal means sealingly engaging said piston and said bore and accommodating the entire movement of said piston from said first position to said second position through elastic deformation.

10. A medication injection device comprising:
    a reusable portion including;
      an electromagnetic solenoid core,
      a solenoid coil, and
      means for energizing said solenoid coil;
    a disposable portion including;
      a reservoir
      a pump chamber, and
      means for altering the volume of said pump chamber,
      said means for altering the volume including an electromagnetic solenoid armature; and means releasably securing said disposable portion to said reusable portion such that said armature is adjacent said core when said disposable portion is secured to said reusable portion, said releasable means including a spring for biasing said disposable portion against said reusable portion to control the stroke length of the armature.

11. A medication injection device comprising:
a reusable portion including:
   an electromagnetic solenoid core having a first alignment surface,
   a solenoid coil, and
   means for energizing said solenoid coil;
a disposable portion including;
   a reservoir, and
   a pump chamber,
means for altering the volume of said pump chamber, said altering means including an electromagnetic solenoid armature and a second alignment surface; and
means for releasably securing said disposable portion to said reusable portion such that the armature is adjacent the core when said disposable porton is secured to said reusable portion, said releasable securing means including a spring for biasing the first alignment surface of said electromagnetic solenoid core against the second alignment surface of said altering means to define the stroke of said armature.

12. The medication injection device of claim 11 wherein said electromagnetic solenoid core includes a first surface for engagement of the armature, said first engagement surface being disposed with respect to the first alignment surface, and wherein said altering means includes a second surface for engagement of the armature, said second engagement surface being disposed with respect to said second alignment surface such that said first and second engagement surfaces define the stroke of said armature.

* * * * *